US00PP20778P2

(12) United States Plant Patent
Lambert et al.

(10) Patent No.: US PP20,778 P2
(45) Date of Patent: Feb. 23, 2010

(54) ***HYDRANGEA* PLANT NAMED 'INH-HYD-14'**

(50) Latin Name: ***Hydrangea* hybrid**
Varietal Denomination: INH-HYD-14

(76) Inventors: Claudie Lambert, Agrocampus Ouest/ INH 2 Rue Andre le Notre, Angers (FR) 49045; Bertrand Hilane, INH 2 Rue Andre le Notre, Angers (FR) 49045

( * ) Notice: Subject to any disclaimer, the term of this patent is extended or adjusted under 35 U.S.C. 154(b) by 0 days.

(21) Appl. No.: 12/290,498

(22) Filed: Oct. 29, 2008

(51) Int. Cl.
*A01H 5/00* (2006.01)

(52) U.S. Cl. ..... Plt./250

(58) Field of Classification Search ..... Plt./250
See application file for complete search history.

*Primary Examiner*—Annette H Para

(57) ABSTRACT

A new and distinct *Hydrangea* cultivar named 'INH-HYD-14' is disclosed, characterized by narrow, pubescent leaves, which are red when young. Large, red hairs on actively growing stems, and a long period before blooming starts. The new variety is a *Hydrangea*, with interesting foliage, suitable for outdoor container and garden purposes.

2 Drawing Sheets

Latin name of the genus and species: *Hydrangea* hybrid.
Variety denomination: 'INH-HYD-14'.

BACKGROUND OF THE INVENTION

The new cultivar is a product of a planned *Hydrangea* breeding program, from the Institut National d'Horticulture located in Angers, France. The new variety was discovered as a seedling within the planned breeding program. This seedling is a result from the crossing made in July 2001 of the female parent, an undistributed proprietary variety referred to as '143' with the male parent, an undistributed proprietary variety referred to as '188.' It was selected by Claudie Lambert and Helene Bertrand during the Summer of 2005 at the research facility in Angers, France.

Asexual reproduction of the new cultivar 'INH-HYD-14' by vegetative cuttings was first performed in Angers, France at the Institut Nation d'Horticulture, during the Spring of 2006 and has shown that the unique features of this cultivar are stable and reproduced true to type on successive generations.

SUMMARY OF THE INVENTION

The cultivar 'INH-HYD-14' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'INH-HYD-14' These characteristics in combination distinguish 'INH-HYD-14' as a new and distinct *Hydrangea* cultivar:

1. Narrow, pubescent leaves.
2. Distinctive red coloration of young foliage.
3. Large red hairs on young, actively growing stems.
4. Long juvenile stage, at least 2 years before flowers appear.
5. Sterile inflorescence without ornamental interest.

PARENTAL COMPARISON

Plants of the new cultivar 'INH-HYD-14' are similar to plants of the female parent, '143,' in most horticultural characteristics, however, plants of the new cultivar 'INH-HYD-14' have pubescent leaves and stems, and unique red coloration of the young foliage. Additionally, plants of the new cultivar are sterile, and form an inflorescence of a different appearance.

'INH-HYD-14' differs from the male parent '188' in having narrower foliage, and having pubescent stems. Additionally, plants of the new cultivar are sterile, and form an inflorescence of a different appearance.

COMMERCIAL COMPARISON

Plants of the new cultivar 'INH-HYD-14' are not comparable to any known commercial varieties.

BRIEF DESCRIPTION OF THE PHOTOGRAPH

Figure 1:
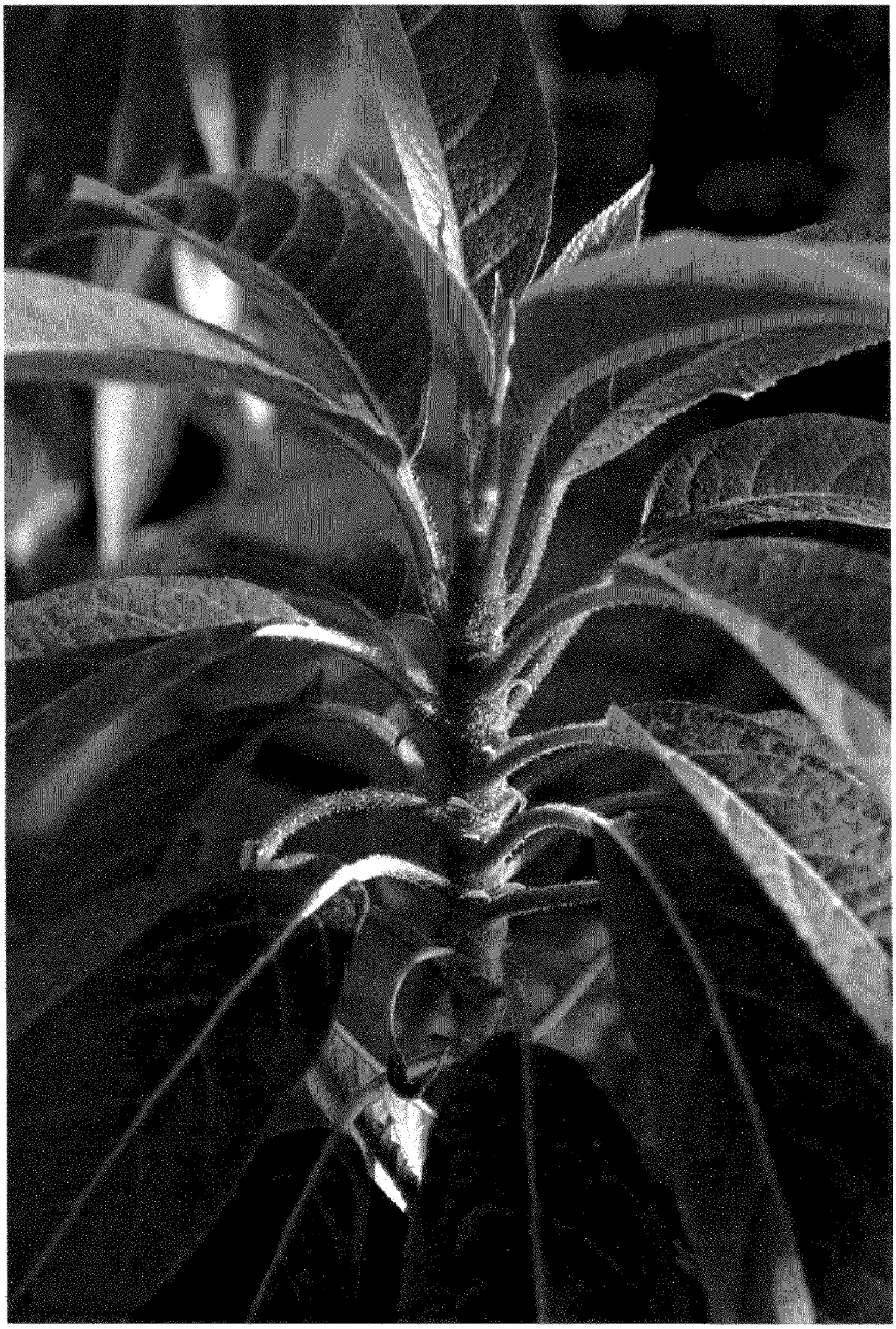

The accompanying photograph in FIG. 1 illustrates in full color typical foliage and stem coloration of 'INH-HYD-14' grown outdoors in Angers, France.

Figure 2:
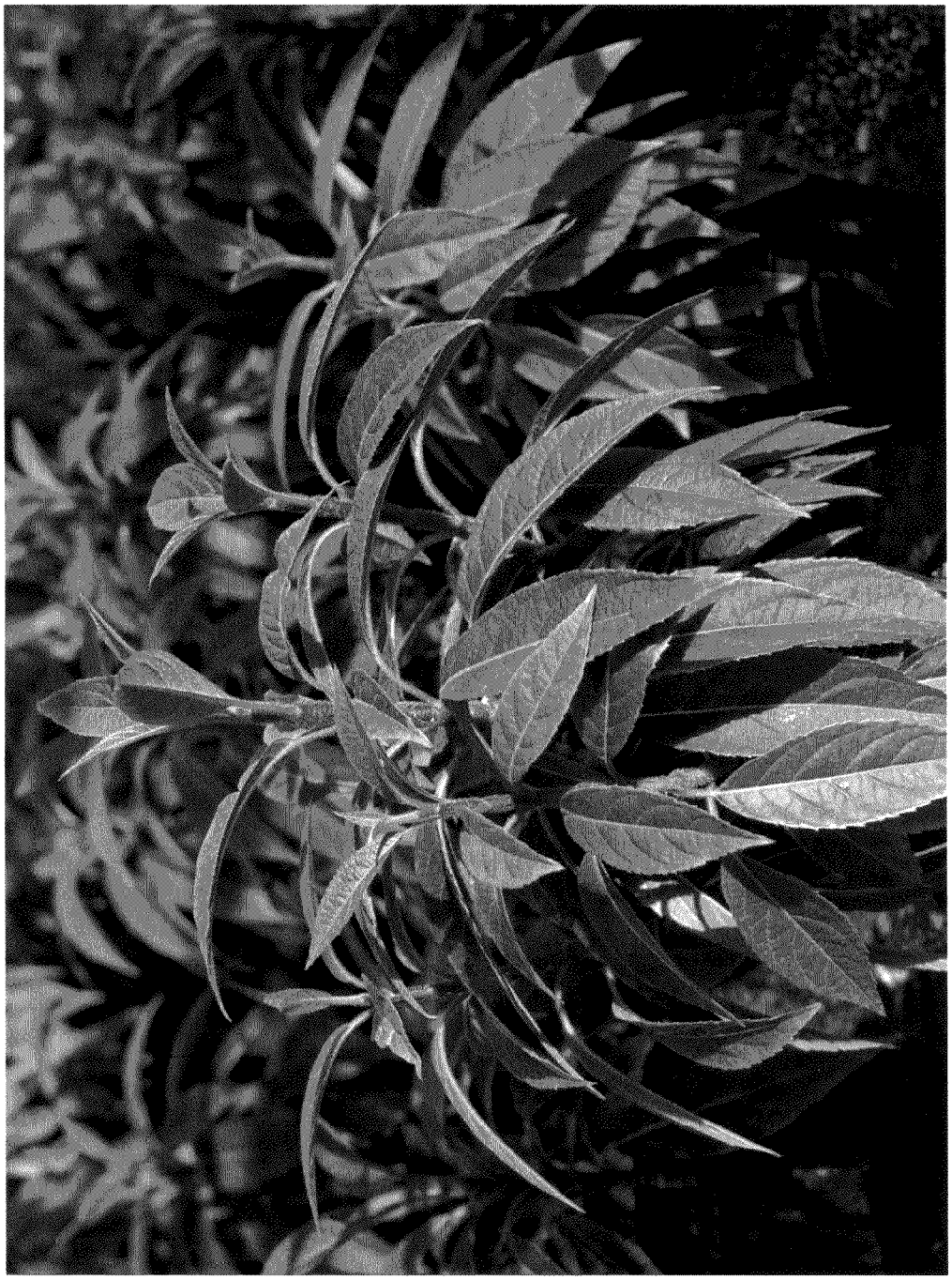

FIG. 2 illustrates plants of the new variety.

The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart except where general terms of ordinary dictionary significance are used. The following observations and measurements describe 'INH-HYD-14' plants outdoors, in Angers, France from October 2006 to October 2008. The growing temperature ranged from 10° C. to 17° C. at night to 12° C. to 35° C. during the day. Measurements and numerical values represent averages of typical flowering types.

Botanical classification: *Hydrangea* hybrid cultivar 'INH-HYD-14.'

PROPAGATION

Time to rooting: 15 to 20 days at approximately 20° C.
Root description: Fine, fibrous, white.

PLANT

Age of the plant described: Approximately 2 years, except for the floral structures. Due to long juvenile stage, floral structures were described from a 4 to 5 year old plant.
Growth habit: Shrub.
Height: Average 27 cm.
Plant spread: Average 45 cm.
Growth rate: About 12 cm/year.
Branching characteristics: Spreading.
Length of lateral branches: Average 18 cm.
Diameter of lateral branches: Approximately 0.6 cm.
Pinching required: No
*Details of pinching.*—No matter.
Lateral branch shape: Spreading
Lateral branch strength: Stout
Lateral branch color: Approximately RHS base Greyed-Orange 174A, top Greyed-Yellow 160B
Other stem or plant characteristics:
*Lenticels.*—Inconspicuous.
*Growing stems.*—Fleshy red pubescence Red 53B.
*Stem pubescence.*—Yes.
Number of leaves per lateral branch: Average 30

FOLIAGE

Leaf:
*Arrangement.*—Opposite.
*Compound or single.*—Single.
*Average length.*—14.2 cm.
*Average width.*—4.7 cm.
*Shape of blade.*—Elliptic.
*Apex.*—Acuminate.
*Base.*—Broadly attenuate.
*Attachment.*—Opposite.
*Margin.*—Entire.
*Texture of top surface.*—Waffled.
*Texture of bottom surface.*—Rough.
*Leaf internode length.*—Approximately 1 cm.
*Color.*—Young foliage upper side: Near R.H.S. Greyed-Red 178B Young foliage under side: Near R.H.S. Greyed-Red 178B Mature foliage upper side: Near R.H.S. Green 138A Mature foliage under side: Near R.H.S. Yellow-Green 147C.
*Venation.*—Type: pinnate Venation color upper side: Near R.H.S. Yellow-Green 147D Venation color under side: Near R.H.S. Yellow-Green 147D with Red-Purple 65B.
*Durability of foliage to stresses.*—Cold tolerance medium.
Petiole:
*Average length.*—3.5 cm.
*Diameter.*—Approximately 0.3 cm.
*Color.*—Near R.H.S. Red 47A.

FLOWER

Age of plant with floral structures: Approximately 6 years.
Bloom period:
*Natural season.*—July and August.
Inflorescence:
*Arrangement.*—Corymbiform.
*Type.*—Lacecap with very few sterile flowers.
*Height.*—Approximately 5 cm.
*Width.*—Approximately 7 cm.
*Quantity of flowers per inflorescence.*—Fertile flowers, approximately >500 Sterile Flowers, approximately 2 or 3.
Bud:
*Bud shape.*—Bumpy.
*Bud length.*—Approximately 0.3 cm.
*Bud diameter.*—Approximately 0.25 cm.
*Bud color.*—Near R.H.S. Greyed-Green 193C Base/calyx: Near R.H.S. Greyed-Green 193D.
Flower:
*Shape.*—Rotate.
*Facing direction.*—Upright.
*Quantity of flowers per lateral stem.*—About 100.
*Quantity of flowers and buds per plant.*—Approximately 1500.
*Diameter of entire flower.*—Fertile: Approximately 0.6 cm. Sterile: Approximately 1 cm.
*Depth of flower.*—Fertile: Approximately 0.1 cm. Sterile: Approximately 0.1 cm.
*Rate of opening.*—Individual flowers: Fully open approximately 2 days from the bud stage. Whole Plant: Approximately 50% of flowers open at once.
*Flower longevity on plant.*—Fertile flowers: Approximately 4 days. Sterile flowers: Approximately 20 days.
*Persistent or self-cleaning.*—Petals self-cleaning.
*Fragrance.*—Very light.
Petals:
*Length of petal.*—Approximately 0.3 cm.
*Width of petal.*—Approximately 0.1 cm.
*Apex.*—Acute and curved.
*Shape of petal.*—Spatulate.
*Petal margin.*—Entire.
*Petal arrangement.*—One whorl.
*Petal number.*—5.
*Petals fused.*—No.
*Petal appearance.*—Dull.
*Petal texture.*—Fleshy.
Color:
*Upper surface at first opening.*—Lighter than RHS Red-Purple 69D.
*Upper surface at maturity.*—Lighter than RHS Red-Purple 69D.
*Upper surface at fading.*—Lighter than RHS Red-Purple 69D.
*Under surface at first opening.*—Lighter than RHS Red-Purple 69D.
*Under surface at maturity.*—Lighter than RHS Red-Purple 69D.
*Under surface at fading.*—Lighter than RHS Red-Purple 69D.
Petaloids: Very few petaloid sepals

CALYX

Present: Yes
Shape: Campanulate
Length: Approximately 0.15 cm
Diameter: Approximately 0.15 cm

SEPAL

Number: 5
Sepal appearance: Dull
Sepal arrangement: One whorl
Sepal length: Approximately 0.05 cm.
Sepal width: Approximately 0.06 cm
Sepal shape: Triangular
Base: Broad
Apex shape: Acute
Margin: Entire
Color: Near R.H.S. Greyed-Green 193D

PEDUNCLE

Length: Approximately 4 cm.
Diameter: Approximately 0.25 cm
Angie: 45°
Strength: Strong
Color: Near R.H.S. Greyed-Green 193C

PEDICEL

Present: Yes
Length: Approximately 1 cm.
Diameter: Approximately 0.15 cm.
Angle: Approximately 50 degrees.
Strength: Stout
Color: Near RHS Greyed-Green 193D

REPRODUCTIVE ORGANS

*Number of pistils per flower.*—2 to 3.
*Pistil length.*—Approximately 0.1 cm.
*Stigma shape.*—Fan-shaped.
*Stigma color.*—Near RHS white 155D.
*Style color.*—Near RHS white 155D.
*Style length.*—Approximately 0.05 cm.
*Ovary color.*—Near RHS white 155D.
*Stamens quantity.*—8 to 10.
*Anther shape.*—Globular.
*Anther size.*—<0.05 cm.
*Anther color.*—Near RHS Red-Purple 69C.
*Pollen color.*—No pollen.

OTHER CHARACTERISTICS

Fruit/seed production: No fruits produced.

Disease resistance: Neither resistance nor susceptibility to diseases or pests has been observed in this variety.

Drought tolerance and cold tolerance: Semi-hardy perennial, tolerant of some high temperatures. Upper limit of temperature tolerance has not been observed, however, known to tolerate temperatures of at least up to 35° C. Lower limits have also not been observed, however, observed hardy to −5° C. No drought tolerance has been observed.

What is claimed is:

1. A new and distinct cultivar of *Hydrangea* plant named 'INH-HYD-14' as herein illustrated and described.

* * * * *